United States Patent
Eckhouse et al.

(10) Patent No.: US 9,271,793 B2
(45) Date of Patent: *Mar. 1, 2016

(54) METHOD AND APPARATUS FOR PERSONAL SKIN TREATMENT

(71) Applicants: Shimon Eckhouse, Haifa (IL); Tuvia Dror Kutscher, Shoham (IL); Boris Vaynberg, Zichron Yaakov (IL)

(72) Inventors: Shimon Eckhouse, Haifa (IL); Tuvia Dror Kutscher, Shoham (IL); Boris Vaynberg, Zichron Yaakov (IL)

(73) Assignee: SYNERON MEDICAL LTD., Yokneam (IL)

(*) Notice: Subject to any disclaimer, the term of this patent is extended or adjusted under 35 U.S.C. 154(b) by 0 days.

This patent is subject to a terminal disclaimer.

(21) Appl. No.: 14/026,523

(22) Filed: Sep. 13, 2013

(65) Prior Publication Data

US 2014/0081250 A1    Mar. 20, 2014

Related U.S. Application Data

(63) Continuation of application No. 12/663,067, filed as application No. PCT/IL2009/000817 on Aug. 20, 2009, now Pat. No. 8,778,003.

(60) Provisional application No. 61/098,774, filed on Sep. 21, 2008, provisional application No. 61/180,901, filed on May 25, 2009.

(51) Int. Cl.
*A61N 5/06* (2006.01)
*A61B 18/20* (2006.01)
(Continued)

(52) U.S. Cl.
CPC .............. *A61B 18/203* (2013.01); *A45D 26/00* (2013.01); *A61B 18/20* (2013.01); *A61B 2018/00005* (2013.01); *A61B 2018/00029* (2013.01); *A61B 2018/00452* (2013.01);
(Continued)

(58) Field of Classification Search
CPC .............................. A61B 18/203; A45D 26/00
See application file for complete search history.

(56) References Cited

U.S. PATENT DOCUMENTS

| | | | |
|---|---|---|---|
| 1,430,354 A | 9/1922 | Burdick | |
| 2,183,726 A | 2/1939 | Sommer et al. | |

(Continued)

FOREIGN PATENT DOCUMENTS

| | | |
|---|---|---|
| CA | 2495005 A1 | 2/2004 |
| CN | 1078383 A | 11/1993 |

(Continued)

OTHER PUBLICATIONS

Written opinion of the international searching authority mailed on Jan. 7, 2010.

(Continued)

*Primary Examiner* — Jessica Stultz
*Assistant Examiner* — Joshua King
(74) *Attorney, Agent, or Firm* — Smith Risley Tempel Santos LLC; Gregory Scott Smith

(57) ABSTRACT

Disclosed is a skin treatment device for personal use. The device includes an optical radiation providing module operating in pulsed or continuous operation mode, a mechanism for continuously displacing the device across the skin, and a device displacement speed monitoring arrangement. When the device is applied to skin, the optical pulses repetition rate establishes the power of the optical radiation as a function of the device displacement speed. The device a hair removal mechanism configured to mechanically remove hair from the treated segment of the skin.

19 Claims, 12 Drawing Sheets

(51) Int. Cl.
*A45D 26/00* (2006.01)
*A61B 18/00* (2006.01)
*A61B 18/18* (2006.01)
*A61B 19/00* (2006.01)

(52) U.S. Cl.
CPC ............... *A61B 2018/00476* (2013.01); *A61B 2018/00636* (2013.01); *A61B 2018/00642* (2013.01); *A61B 2018/1807* (2013.01); *A61B 2019/4815* (2013.01)

(56) References Cited

U.S. PATENT DOCUMENTS

| | | | |
|---|---|---|---|
| 2,231,095 A | 2/1941 | Sommer et al. | |
| 2,824,308 A | 2/1958 | Duncan | |
| 2,888,927 A | 6/1959 | Fozard | |
| 3,088,205 A | 5/1963 | Ellis | |
| D196,532 S | 10/1963 | Facci | |
| 4,174,713 A | 11/1979 | Mehl | |
| 4,182,329 A | 1/1980 | Smit et al. | |
| 4,185,632 A | 1/1980 | Shaw | |
| 4,200,104 A | 4/1980 | Harris | |
| 4,211,230 A | 7/1980 | Woltosz | |
| 4,321,926 A | 3/1982 | Roge | |
| D269,294 S | 6/1983 | Rakocy et al. | |
| D271,015 S | 10/1983 | Geraets | |
| D271,199 S | 11/1983 | Geraets | |
| 4,444,190 A * | 4/1984 | Mutzhas | A61N 5/0621 250/503.1 |
| D274,462 S | 6/1984 | Rakocy et al. | |
| 4,532,924 A | 8/1985 | Auth et al. | |
| 4,550,728 A | 11/1985 | Runyon et al. | |
| 4,553,936 A | 11/1985 | Wang | |
| 4,566,454 A | 1/1986 | Mehl et al. | |
| 4,630,182 A * | 12/1986 | Moroi | F21V 29/83 362/294 |
| 4,686,986 A | 8/1987 | Fenyo et al. | |
| 4,753,958 A | 6/1988 | Weinstein et al. | |
| 4,784,135 A | 11/1988 | Blum et al. | |
| 4,844,063 A | 7/1989 | Clark | |
| 4,867,682 A | 9/1989 | Hammesfahr et al. | |
| 4,869,584 A | 9/1989 | Dion | |
| 4,940,456 A | 7/1990 | Sibalis et al. | |
| 4,979,180 A | 12/1990 | Muncheryan | |
| 5,016,999 A | 5/1991 | Williams | |
| 5,087,240 A | 2/1992 | Sibalis | |
| 5,125,928 A | 6/1992 | Parins et al. | |
| 5,158,537 A | 10/1992 | Haak et al. | |
| 5,169,384 A | 12/1992 | Bosniak et al. | |
| 5,250,023 A | 10/1993 | Lee et al. | |
| 5,286,479 A | 2/1994 | Garlich et al. | |
| 5,316,473 A | 5/1994 | Hare | |
| 5,348,554 A | 9/1994 | Imran et al. | |
| 5,383,874 A | 1/1995 | Jackson et al. | |
| 5,402,697 A | 4/1995 | Brooks | |
| 5,406,340 A | 4/1995 | Hoff | |
| 5,418,130 A | 5/1995 | Platz et al. | |
| 5,487,662 A | 1/1996 | Kipke et al. | |
| 5,509,916 A | 4/1996 | Taylor | |
| 5,520,684 A | 5/1996 | Imran | |
| 5,521,392 A | 5/1996 | Kennedy et al. | |
| 5,582,476 A | 12/1996 | Hansen | |
| 5,611,793 A | 3/1997 | Wilson et al. | |
| 5,642,997 A | 7/1997 | Gregg et al. | |
| 5,658,148 A | 8/1997 | Neuberger et al. | |
| 5,674,191 A | 10/1997 | Edwards et al. | |
| 5,681,282 A | 10/1997 | Eggers et al. | |
| 5,683,380 A * | 11/1997 | Eckhouse | A61B 18/203 606/10 |
| 5,693,052 A | 12/1997 | Weaver | |
| 5,698,866 A | 12/1997 | Doiron et al. | |
| 5,704,935 A | 1/1998 | Pahl et al. | |
| 5,707,403 A | 1/1998 | Grove et al. | |
| 5,718,702 A | 2/1998 | Edwards | |
| 5,722,411 A | 3/1998 | Suzuki et al. | |
| 5,735,844 A | 4/1998 | Anderson et al. | |
| 5,769,880 A | 6/1998 | Truckai et al. | |
| 5,776,092 A | 7/1998 | Farin et al. | |
| 5,814,008 A | 9/1998 | Chen et al. | |
| 5,824,023 A | 10/1998 | Anderson | |
| 5,836,999 A | 11/1998 | Eckhouse et al. | |
| 5,843,143 A | 12/1998 | Whitehurst | |
| 5,846,252 A | 12/1998 | Mehl, Sr. | |
| 5,868,744 A | 2/1999 | Willmen | |
| 5,871,469 A | 2/1999 | Eggers et al. | |
| 5,873,855 A | 2/1999 | Eggers et al. | |
| 5,888,198 A | 3/1999 | Eggers et al. | |
| 5,935,143 A | 8/1999 | Hood | |
| 5,949,514 A | 9/1999 | Wargon | |
| 5,954,710 A | 9/1999 | Paolini et al. | |
| 5,961,482 A | 10/1999 | Chien et al. | |
| 5,961,543 A * | 10/1999 | Waldmann | 607/88 |
| 5,983,130 A | 11/1999 | Phipps et al. | |
| 5,983,135 A | 11/1999 | Avrahami | |
| 5,984,915 A | 11/1999 | Loeb et al. | |
| 5,993,180 A | 11/1999 | Westerhof et al. | |
| 6,024,733 A | 2/2000 | Eggers et al. | |
| 6,030,384 A | 2/2000 | Nezhat | |
| 6,042,959 A | 3/2000 | Debe et al. | |
| 6,056,548 A | 5/2000 | Neuberger et al. | |
| 6,063,108 A | 5/2000 | Salansky et al. | |
| 6,066,134 A | 5/2000 | Eggers et al. | |
| 6,078,830 A | 6/2000 | Levin et al. | |
| 6,080,127 A | 6/2000 | Li et al. | |
| 6,080,391 A | 6/2000 | Tsuchiya et al. | |
| 6,081,934 A | 7/2000 | Stefanovsky et al. | |
| 6,097,976 A | 8/2000 | Yang et al. | |
| 6,107,326 A | 8/2000 | Jori | |
| 6,132,701 A | 10/2000 | Perez et al. | |
| 6,148,232 A | 11/2000 | Avrahami | |
| 6,159,222 A | 12/2000 | Yiu | |
| 6,173,202 B1 | 1/2001 | Eppstein et al. | |
| 6,187,001 B1 * | 2/2001 | Azar et al. | 606/9 |
| 6,190,609 B1 | 2/2001 | Chapman et al. | |
| 6,191,110 B1 | 2/2001 | Jaynes et al. | |
| 6,208,881 B1 | 3/2001 | Champeau | |
| 6,210,402 B1 | 4/2001 | Olsen et al. | |
| 6,221,095 B1 | 4/2001 | Van Zuylen et al. | |
| 6,223,071 B1 * | 4/2001 | Lundahl et al. | 600/476 |
| 6,231,571 B1 | 5/2001 | Ellman et al. | |
| 6,231,593 B1 | 5/2001 | Meserol | |
| 6,251,127 B1 | 6/2001 | Biel | |
| 6,256,525 B1 | 7/2001 | Yang et al. | |
| 6,258,319 B1 | 7/2001 | Hearst et al. | |
| 6,273,884 B1 | 8/2001 | Altshuler et al. | |
| 6,275,728 B1 | 8/2001 | Venkatraman | |
| 6,277,116 B1 | 8/2001 | Utely et al. | |
| 6,280,438 B1 | 8/2001 | Eckhouse et al. | |
| 6,288,498 B1 | 9/2001 | Cheng | |
| 6,302,874 B1 | 10/2001 | Zhang et al. | |
| 6,308,413 B1 | 10/2001 | Westerhof et al. | |
| 6,325,797 B1 | 12/2001 | Stewart et al. | |
| 6,343,400 B1 | 2/2002 | Massholder et al. | |
| 6,343,933 B1 | 2/2002 | Montgomery et al. | |
| 6,374,653 B1 | 4/2002 | Gokcebay et al. | |
| 6,400,976 B1 | 6/2002 | Champeau | |
| 6,406,157 B1 | 6/2002 | Audet | |
| 6,413,255 B1 | 7/2002 | Stern | |
| 6,413,268 B1 | 7/2002 | Hartman | |
| 6,419,674 B1 | 7/2002 | Bowser et al. | |
| 6,433,343 B1 | 8/2002 | Cimino et al. | |
| 6,440,121 B1 | 8/2002 | Weber et al. | |
| 6,461,354 B1 | 10/2002 | Olsen et al. | |
| 6,461,567 B1 | 10/2002 | Hearst et al. | |
| 6,462,070 B1 | 10/2002 | Hasan et al. | |
| 6,471,716 B1 | 10/2002 | Pecukonis | |
| 6,477,410 B1 | 11/2002 | Henley et al. | |
| 6,482,201 B1 | 11/2002 | Olsen et al. | |
| 6,482,204 B1 | 11/2002 | Lax et al. | |
| 6,487,447 B1 | 11/2002 | Weimann et al. | |
| 6,490,482 B2 | 12/2002 | Mori et al. | |
| 6,493,940 B2 | 12/2002 | Westerhof et al. | |
| 6,494,900 B1 | 12/2002 | Salansky et al. | |
| 6,497,702 B1 | 12/2002 | Bernaz | |

(56) References Cited

U.S. PATENT DOCUMENTS

| | | | |
|---|---|---|---|
| 6,508,813 B1 | 1/2003 | Altshuler | |
| 6,510,341 B1 | 1/2003 | Kuribayashi et al. | |
| 6,511,475 B1 | 1/2003 | Altshuler et al. | |
| 6,514,243 B1 * | 2/2003 | Eckhouse | A61B 18/203 606/10 |
| 6,514,248 B1 | 2/2003 | Eggers et al. | |
| 6,517,532 B1 | 2/2003 | Altshuler et al. | |
| 6,533,775 B1 | 3/2003 | Rizoiu | |
| 6,544,259 B1 | 4/2003 | Tsaliovich | |
| 6,544,261 B2 | 4/2003 | Ellsberry et al. | |
| 6,558,411 B1 * | 5/2003 | Steen | 607/88 |
| 6,558,653 B2 | 5/2003 | Andersen et al. | |
| 6,572,637 B1 | 6/2003 | Yamazaki et al. | |
| 6,582,429 B2 | 6/2003 | Krishnan et al. | |
| 6,594,905 B2 | 7/2003 | Furst et al. | |
| 6,595,947 B1 | 7/2003 | Mikszta et al. | |
| 6,595,990 B1 | 7/2003 | Weinstein et al. | |
| 6,597,946 B2 | 7/2003 | Avrahami et al. | |
| 6,602,245 B1 | 8/2003 | Thiberg | |
| 6,611,706 B2 | 8/2003 | Avrahami et al. | |
| 6,611,707 B1 | 8/2003 | Prausnitz et al. | |
| 6,612,819 B1 | 9/2003 | Furst et al. | |
| 6,615,079 B1 | 9/2003 | Avrahami | |
| 6,618,620 B1 | 9/2003 | Freundlich et al. | |
| 6,620,158 B2 | 9/2003 | Ronci | |
| 6,623,454 B1 | 9/2003 | Eggers et al. | |
| 6,629,974 B2 | 10/2003 | Penny et al. | |
| 6,632,002 B1 | 10/2003 | Chubb et al. | |
| 6,632,193 B1 | 10/2003 | Davison et al. | |
| 6,632,220 B1 | 10/2003 | Eggers et al. | |
| 6,637,877 B1 | 10/2003 | Hartley et al. | |
| 6,659,106 B1 | 12/2003 | Hovda et al. | |
| 6,663,620 B2 | 12/2003 | Altshuler et al. | |
| 6,676,655 B2 | 1/2004 | McDaniel | |
| 6,678,554 B1 | 1/2004 | Sun et al. | |
| 6,702,808 B1 | 3/2004 | Kreindel | |
| 6,708,060 B1 | 3/2004 | Avrahami et al. | |
| 6,711,435 B2 | 3/2004 | Avrahami | |
| 6,719,754 B2 | 4/2004 | Underwood et al. | |
| 6,723,092 B2 | 4/2004 | Brown et al. | |
| D490,156 S | 5/2004 | Fischer et al. | |
| D490,526 S | 5/2004 | Jonsen | |
| 6,740,079 B1 | 5/2004 | Eggers et al. | |
| 6,743,211 B1 | 6/2004 | Prausnitz et al. | |
| 6,758,845 B1 | 7/2004 | Weckwerth et al. | |
| 6,761,729 B2 | 7/2004 | Babaev | |
| 6,767,341 B2 | 7/2004 | Cho | |
| 6,770,069 B1 | 8/2004 | Hobart et al. | |
| 6,773,431 B2 | 8/2004 | Eggers et al. | |
| 6,780,838 B2 | 8/2004 | Lipton et al. | |
| RE38,643 E | 11/2004 | Sugaya et al. | |
| 6,887,260 B1 | 5/2005 | McDaniel | |
| 6,905,496 B1 | 6/2005 | Ellman et al. | |
| 6,974,450 B2 | 12/2005 | Weber et al. | |
| 7,006,874 B2 | 2/2006 | Knowlton et al. | |
| 7,022,121 B2 | 4/2006 | Stern et al. | |
| 7,077,840 B2 | 7/2006 | Altshuler et al. | |
| 7,097,656 B1 * | 8/2006 | Akopov et al. | 607/90 |
| 7,115,123 B2 | 10/2006 | Knowlton et al. | |
| 7,118,563 B2 | 10/2006 | Weckwerth et al. | |
| 7,141,049 B2 | 11/2006 | Stern et al. | |
| 7,153,298 B1 | 12/2006 | Cohen | |
| 7,234,239 B2 | 6/2007 | Saito et al. | |
| 7,238,183 B2 | 7/2007 | Kreindel | |
| 7,251,531 B2 | 7/2007 | Mosher et al. | |
| 7,252,678 B2 * | 8/2007 | Ostler et al. | 607/88 |
| 7,275,819 B2 | 10/2007 | Bleau | |
| 7,278,993 B2 | 10/2007 | Kelly et al. | |
| 7,435,247 B2 | 10/2008 | Woloszko et al. | |
| 7,494,488 B2 | 2/2009 | Weber | |
| 7,517,344 B2 | 4/2009 | Van Hal et al. | |
| 7,643,874 B2 | 1/2010 | Nitzan et al. | |
| 7,713,266 B2 | 5/2010 | Elkins et al. | |
| 7,771,419 B2 | 8/2010 | Carmel et al. | |
| 7,824,394 B2 | 11/2010 | Manstein | |
| 7,935,107 B2 | 5/2011 | Altshuler et al. | |
| 7,963,985 B2 * | 6/2011 | Minamoto et al. | 607/94 |
| 7,988,312 B2 * | 8/2011 | Matui | 362/96 |
| 8,021,360 B2 | 9/2011 | Dunning et al. | |
| 8,034,052 B2 | 10/2011 | Podhajsky | |
| 8,109,927 B2 | 2/2012 | Kelly et al. | |
| 8,128,622 B2 | 3/2012 | Podhajsky et al. | |
| 8,133,191 B2 | 3/2012 | Rosenberg et al. | |
| 8,133,216 B2 | 3/2012 | Knopp et al. | |
| 8,157,807 B2 | 4/2012 | Ferren et al. | |
| 8,202,268 B1 | 6/2012 | Wells et al. | |
| 8,206,381 B2 | 6/2012 | Lischinsky et al. | |
| 8,235,989 B2 | 8/2012 | Palanker et al. | |
| 8,273,037 B2 | 9/2012 | Kreindel et al. | |
| 8,292,882 B2 | 10/2012 | Danek et al. | |
| 8,506,564 B2 | 8/2013 | Long et al. | |
| 8,778,003 B2 * | 7/2014 | Eckhouse et al. | 607/90 |
| 2001/0007068 A1 | 7/2001 | Ota et al. | |
| 2001/0014819 A1 | 8/2001 | Ingle et al. | |
| 2002/0010414 A1 | 1/2002 | Coston et al. | |
| 2002/0035363 A1 | 3/2002 | Edwards et al. | |
| 2002/0058936 A1 | 5/2002 | Avrahami et al. | |
| 2002/0082543 A1 | 6/2002 | Park et al. | |
| 2002/0104543 A1 | 8/2002 | Hollander et al. | |
| 2002/0120256 A1 | 8/2002 | Furuno et al. | |
| 2002/0120260 A1 | 8/2002 | Morris et al. | |
| 2002/0120261 A1 | 8/2002 | Morris et al. | |
| 2002/0128641 A1 | 9/2002 | Underwood et al. | |
| 2002/0128648 A1 | 9/2002 | Weber et al. | |
| 2002/0161324 A1 | 10/2002 | Henley et al. | |
| 2002/0173780 A1 * | 11/2002 | Altshuler | A61B 18/203 606/9 |
| 2002/0183245 A1 | 12/2002 | Hasan et al. | |
| 2002/0190337 A1 | 12/2002 | House et al. | |
| 2002/0193729 A1 | 12/2002 | Cormier et al. | |
| 2002/0198575 A1 | 12/2002 | Sullivan | |
| 2003/0004499 A1 | 1/2003 | McDaniel | |
| 2003/0018255 A1 | 1/2003 | Martin et al. | |
| 2003/0032950 A1 | 2/2003 | Altshuler et al. | |
| 2003/0055413 A1 | 3/2003 | Altshuler et al. | |
| 2003/0055414 A1 | 3/2003 | Altshuler et al. | |
| 2003/0109871 A1 | 6/2003 | Johnson et al. | |
| 2003/0135250 A1 | 7/2003 | Lauman et al. | |
| 2003/0185255 A1 | 10/2003 | Ye et al. | |
| 2003/0195494 A1 | 10/2003 | Altshuler et al. | |
| 2003/0199863 A1 | 10/2003 | Swanson et al. | |
| 2003/0199946 A1 | 10/2003 | Gutwein | |
| 2004/0010250 A1 | 1/2004 | Manna et al. | |
| 2004/0010298 A1 | 1/2004 | Altshuler et al. | |
| 2004/0015161 A1 | 1/2004 | Lovewell | |
| 2004/0015162 A1 | 1/2004 | McGaffigan | |
| 2004/0064167 A1 | 4/2004 | Berry et al. | |
| 2004/0133251 A1 | 7/2004 | Altshuler et al. | |
| 2004/0138603 A1 | 7/2004 | Cleary et al. | |
| 2004/0143308 A1 | 7/2004 | Lundahl | |
| 2004/0167501 A1 | 8/2004 | Island et al. | |
| 2004/0181216 A1 | 9/2004 | Kelly et al. | |
| 2004/0193234 A1 | 9/2004 | Butler | |
| 2004/0210214 A1 | 10/2004 | Knowlton | |
| 2004/0225339 A1 * | 11/2004 | Yaroslavsky et al. | 607/88 |
| 2004/0236269 A1 * | 11/2004 | Marchitto et al. | 604/22 |
| 2004/0236320 A1 | 11/2004 | Protsenko et al. | |
| 2004/0260210 A1 | 12/2004 | Ella et al. | |
| 2004/0267252 A1 | 12/2004 | Washington et al. | |
| 2005/0015042 A1 | 1/2005 | Sun et al. | |
| 2005/0033286 A1 | 2/2005 | Eggers et al. | |
| 2005/0043653 A1 | 2/2005 | Trimmer et al. | |
| 2005/0049543 A1 | 3/2005 | Anderson et al. | |
| 2005/0085804 A1 | 4/2005 | McGaffigan | |
| 2005/0096646 A1 | 5/2005 | Wellman et al. | |
| 2005/0137654 A1 | 6/2005 | Hoenig et al. | |
| 2005/0137655 A1 | 6/2005 | MacFarland et al. | |
| 2005/0143793 A1 | 6/2005 | Korman et al. | |
| 2005/0147137 A1 | 7/2005 | Slatkine | |
| 2005/0149012 A1 * | 7/2005 | Penny et al. | 606/41 |
| 2005/0177139 A1 * | 8/2005 | Yamazaki et al. | 606/9 |
| 2005/0288680 A1 | 12/2005 | Ingle et al. | |
| 2006/0036300 A1 | 2/2006 | Kreindel | |
| 2006/0058712 A1 | 3/2006 | Altshuler et al. | |

(56) References Cited

U.S. PATENT DOCUMENTS

| | | |
|---|---|---|
| 2006/0130675 A1 | 6/2006 | Crawford |
| 2006/0200213 A1 | 9/2006 | McDaniel |
| 2006/0231568 A1 | 10/2006 | Lynn et al. |
| 2006/0247741 A1 | 11/2006 | Hsu et al. |
| 2006/0253112 A1 | 11/2006 | Suarez et al. |
| 2006/0271028 A1 | 11/2006 | Altshuler et al. |
| 2007/0009542 A1 | 1/2007 | Levin et al. |
| 2007/0016117 A1 | 1/2007 | Sliwa et al. |
| 2007/0038206 A1 | 2/2007 | Altshuler et al. |
| 2007/0093798 A1 | 4/2007 | Debenedictis et al. |
| 2007/0106349 A1 | 5/2007 | Karni et al. |
| 2007/0129711 A1* | 6/2007 | Altshuler et al. ............ 606/9 |
| 2007/0129771 A1 | 6/2007 | Kurtz et al. |
| 2007/0142881 A1 | 6/2007 | Hennings |
| 2007/0191821 A1 | 8/2007 | Wachler |
| 2007/0191827 A1 | 8/2007 | Lischinsky et al. |
| 2007/0197895 A1 | 8/2007 | Nycz et al. |
| 2007/0198004 A1 | 8/2007 | Altshuler et al. |
| 2007/0213696 A1 | 9/2007 | Altshuler et al. |
| 2007/0239142 A1 | 10/2007 | Altshuler et al. |
| 2007/0239143 A1 | 10/2007 | Altshuler et al. |
| 2007/0239152 A1 | 10/2007 | Trezon |
| 2007/0271714 A1 | 11/2007 | Adam et al. |
| 2008/0004678 A1 | 1/2008 | Kreindel |
| 2008/0123238 A1 | 5/2008 | Campos et al. |
| 2008/0139974 A1 | 6/2008 | Da Silva |
| 2008/0183167 A1 | 7/2008 | Britva et al. |
| 2008/0188846 A1 | 8/2008 | Palanker et al. |
| 2008/0200910 A1 | 8/2008 | Burger et al. |
| 2008/0214986 A1 | 9/2008 | Ivorra et al. |
| 2008/0214988 A1 | 9/2008 | Altshuler et al. |
| 2008/0215124 A1 | 9/2008 | Wagenaar et al. |
| 2008/0221504 A1 | 9/2008 | Aghion |
| 2008/0274166 A1 | 11/2008 | Sacks et al. |
| 2008/0294153 A1 | 11/2008 | Altshuler et al. |
| 2008/0306476 A1 | 12/2008 | Hennings et al. |
| 2009/0034263 A1* | 2/2009 | Stenback ............ F21V 15/01 362/296.01 |
| 2009/0036953 A1 | 2/2009 | Gustavsson |
| 2009/0043293 A1 | 2/2009 | Pankratov et al. |
| 2009/0105706 A1 | 4/2009 | Livneh |
| 2009/0112205 A1 | 4/2009 | McGill et al. |
| 2009/0171341 A1 | 7/2009 | Pope et al. |
| 2009/0182315 A1 | 7/2009 | Zigan et al. |
| 2009/0192503 A1 | 7/2009 | Epshtein et al. |
| 2009/0222023 A1 | 9/2009 | Boone et al. |
| 2009/0234341 A1 | 9/2009 | Roth |
| 2009/0234342 A1 | 9/2009 | Ely et al. |
| 2009/0299361 A1 | 12/2009 | Flyash et al. |
| 2009/0306636 A1* | 12/2009 | Ben-Israel et al. ............ 606/9 |
| 2010/0010480 A1 | 1/2010 | Mehta et al. |
| 2010/0145321 A1 | 6/2010 | Altshuler et al. |
| 2010/0185193 A1 | 7/2010 | Kreindel |
| 2010/0198134 A1 | 8/2010 | Eckhouse |
| 2010/0211055 A1 | 8/2010 | Eckhouse et al. |
| 2010/0249772 A1 | 9/2010 | Mehta et al. |
| 2011/0015549 A1 | 1/2011 | Eckhouse et al. |
| 2011/0166559 A1 | 7/2011 | Eckhouse et al. |
| 2011/0196363 A1 | 8/2011 | Kreindel |
| 2012/0016354 A9 | 1/2012 | Epshtein et al. |
| 2012/0022435 A1 | 1/2012 | Ignon et al. |
| 2012/0022504 A1 | 1/2012 | Epshtein et al. |
| 2012/0022512 A1 | 1/2012 | Vaynberg |
| 2012/0022518 A1 | 1/2012 | Levinson |
| 2012/0123397 A1 | 5/2012 | Epshtein et al. |
| 2012/0143178 A9 | 6/2012 | Mehta |
| 2012/0197242 A1 | 8/2012 | Rosenberg |
| 2012/0290023 A1 | 11/2012 | Boyden et al. |
| 2013/0144280 A1 | 6/2013 | Eckhouse et al. |
| 2013/0289679 A1 | 10/2013 | Eckhouse et al. |

FOREIGN PATENT DOCUMENTS

| | | |
|---|---|---|
| EP | 0743029 B1 | 7/2002 |
| EP | 0824019 B1 | 11/2002 |
| GB | 2125986 A | 8/1982 |
| GB | 2202442 A | 9/1988 |
| JP | 04299998 A2 | 10/1992 |
| JP | 06113920 A2 | 4/1994 |
| JP | 11132843 A2 | 12/1999 |
| JP | 2003034630 | 2/2003 |
| WO | WO-93/21992 A1 | 11/1993 |
| WO | WO-9909143 A1 | 2/1999 |
| WO | WO-02078644 A2 | 10/2002 |
| WO | WO-03039367 A1 | 5/2003 |
| WO | WO 2007137304 A2 | 11/2007 |

OTHER PUBLICATIONS

Acne Clearance, LHE Clinical Casebook, Radiancy: Lighting the Future of Skin Care, ©2002.

Acne Star web page, describing "How to use get rid of Acne Treatment", printed May 5, 2005.

Acne Star web page, describing Clinical Studies, "The Treatment of acne vulgaris with a novel device that uses Gallium—Nitride diode light", printed May 5, 2005.

Aesthetic Buyers Guide: The Leading Cosmetic Practice Resource, Jan./Feb. 2004, vol. 7, No. I.

Bollen, CM. et al., "Full- versus partial-mouth disinfection in the treatment of periodontal infections. A pilot study: long-term microbiological observations". J Clin Periodontol Oct. 23, 1996(10):960-70 (Abstract).

Bollen, CM. et al., "The effect of a one-stage full-mouth disinfection on different intra-oral niches. Clinical and microbiological observations", J Clin Periodontol Jan. 25, 1998(1 ):56-66 (Abstract).

Calder1-IEAD, R. Glen, "The Photobiology of LED Phototherapy".

Charakida et al., "Phototherapy in the Treatment of Acne Vulgaris, What is the Role'?", Am. J. Clin. Dermatol 2004: 5(4): 211-216.

Cohen LR., "What causes bad breath?", University of Toronto; webpage (printed before Nov. 2, 2004).

Coventry et al. (2000) "ABC of oral health: Periodontal disease" British Medical Journal, 321, 36-39.

De Soete, M. et al., "One-stage full-mouth disinfection. Long-term microbiological results analyzed by checker board DNA-DNA hybridization", J Periodontol Mar. 2001; 72(3):374-82 (Abstract).

Elman M. et al., "The effective treatment of acne vulgaris by a high-intensity, narrow bank 405-420 nm light source", Cosmetic & Laser Ther 2003; 5: 111-116.

Flow Control Network web page, "Mini Diaphragm Pumps for Precision Dispensing" by Ping Lin, printed Aug. 2, 2005.

Friedberg JS et al., "Antibody-Targeted Photolysis Bacteriocidal Effects of Sn (IV) Chlonn e6-Dextran-Monoclonal Antibody Conjugates", Annals New York Academy of Sciences 618:383-393, 1991.

Greenstein G., Full-mouth therapy versus individual quadrant root planning: a critical commentary, JPeriodontol Jul. 2002;73(7):797-812 (Abstract).

Hamblin, M. et al., "Rapid Control of Wound Infections by Targeted Photodynamic Therapy Monitored by In Vivo Bioluminescence Imagining", Photochemistry and Photobiology, 2002, 75(1 ): 51-57.

Komerik et al. (2003) "In vivo killing of Porphyromonas gingivalis by toluidine blue-mediated photosensitization in an animal model" Antimicrobial Agents and Chemotherapy, 47(3), 932-940.

Krespi, et al. (2005) "Lethal photosensitization of oral pathogens via red-filtered halogen larnp" Oral Diseases, 11(S1 ), 92-95.

Malik, Z. et al., "New Trends in Photobiology (Invited Review) Bactericidal Effects of Photoactivated Porphyrins—An Alternative Approach to Antimicrobial Drugs", Journal of Photochemistry and Photobiology, B: Biology, 5_1_1990}_281-293.

Matevski D. et al., "Lethal photosensitization of periodontal pathogens by a red-filtered Xenon lamp in invitro", JPeriodont. Res. 2003. 38:428-435.

Matevski D. et al., "Sensitivity of Porphyromonas gingivalis to Light-Activated Toluidine Blue O", University of Toronto, Faculty of Dentistry; Slide presentation (presented before Nov. 15, 2002).

(56) References Cited

OTHER PUBLICATIONS

Meisel etal. (2005) "Photodynamic therapy for periodontal diseases: State of the are" J. Photochem. Photobiol., 79, 159-170.

Mongardini, C. et al., "One stage full-versus partial-mouth disinfection in the treatment of chronic adult or generalized early-onset periodontitis. I. Long-term clinical observations", J Periodontol Jun. 1999;70(6):632-45 1Abstrac!2.

Morton C.A. et al., An open study to determine the efficacy of blue light in the treatment of mild to moderate acne: preliminary data (publication status unknown).

Nakano et al. (2002) "Correlation between oral malodor and periodontal bacteria" Microbes Infect., 4(6), 679-683.

Ondine Biopharma web page—printed Oct. 15, 2002.

Papageorgiou ct al., "Phototherapy with blue (415 nm) and red (660 nm) light in the treatment of acne vulgaris", British Journal of Dermatology 2000: 142: 973-978.

Pharmaceutical description, Levulan® Kerastick *arninolevulinic acid I-IC!) for Topical Solution, 20'X.

Quirynen, M. et al. "Full- vs. partial-mouth disinfection in the treatment of periodontal infections: short-term clinical and microbiological observations", J Dent Res Aug. 1995;74(8):1459-67 (Abstract).

Quirynen, M. et al., "The effect of a 1-stage full-mouth disinfection on oral malodor and microbial colonization of the tongue in periodontitis. A pilot study", J Periodontol Mar. 1998;69(3):374-82 (Abstract).

Quirynen, M. et al., "The intra-oral translocation of periodontopathogens jeopardises the outcome of periodontal therapy", Journal of Clincial Periodontology, Jun. 2001, vol. 28, Issue 6, p. 499 (Abstract).

Quirynen, M. et al., "The role of chlorhexidine in the one-stage full-mouth disinfection treatment of patients with advanced adult periodontitis. Long-term clinical and microbiological observations", J Clin Periodontol 2000 Al!JL2~579-89 J__Abstrac_!).

Quirynen. M. et al., "One stage full- versus partial-mouth disinfection in the treatment of chronic adult or generalized early-onset periodontitis. II. Long-term impact on microbial load", J Periodontol Jun. 1999;70(6):646-56 J__Abstrac!2.

Sanz et al. (2001) "Fundamentals of breath malodour" Journal of Contemporary Dental Practice, 2(4), 1-13.

Sarkar et al. (1993) "Lethal photosensitization of bacteria in subgingival plaque from patients with chronic periodontitis" J. Periodont. Res , 28, 204-21 O.

Skin91 I .corn web page regarding Peter Thomas Roth Clinical Acne Medication, acne treatrnent-Benzoyl Peroxide 5% pbp5, printed Apr. 19, 2005.

Soukos et al. (1998) "Targeted antimicrobial photochemotherapy", Antimicrobial Agents and Chemotherapy 42( 10 ), 2595-2601.

Spire Awarded Contract for Ear Surgery Laser—Press Release Aug. 23, 2002.

Temperatures.corn web page, "Thermistor Temperature Sensors," printed Aug. 2, 200.

Vandekerckhove, BN. et al.. "Full- versus partial-mouth disinfection in the treatment of periodontal infections. Long-term clinical observations of a pilot study", J Periodontol Dec. 1996;67(12):1251-9 (Abstract).

Wainwright M., Photodynamic antimicrobial chemotherapy (PACT), Journal of Antimicrobial Chemotherapy (1998)42, 13-28.

Wilson (2005) "Lethal photosensitisation of oral bacteria and its potential application in the photodynamic therapy of oral infection" Photochem. Photobiol. Sci., 3, 412-418.

Wilson et al. (1995) "Bacteria in supragingival plaque samples can be killed by low-power laser light in the presence of a photosensitizer" J. Appl. Bacteriol., 78, 569-574.

Wood, et al. (1999) "An in vitro study of the use of photodynamic therapy for the treatment of natural oral plaque biofilms formed in vivo" J. Photochem. Photogiol. B: Biol., 50, 1-7.

www.lightbioscience.com web page, Gentle Waves Cosmcceuticals, printed Jul. 29, 200.

www.lightbioscience.com web page, Gentle Waves LED Photomodulation Fact Sheet, printed Jul. 29, 2005.

PCT/IL08/01612 International Search Report.
PCT/IL09/00695 International Search Report.
PCT/IL09/00817 International Search Report.
PCT/IL09/00856 International Search Report.
PCT/IL10/00222 International Search Report.
PCT/IL2010/001025 International Search Report.

* cited by examiner

METHOD AND APPARATUS FOR PERSONAL SKIN TREATMENT

CROSS-REFERENCE TO RELATED APPLICATIONS

This is a non-provisional application filed in the United States Patent Office under 37 CFR 1.53(b) and 35 U.S.C. 111 as a continuation of the U.S. patent application Ser. No. 12/663,067 filed on Apr. 4, 2009, which application is a continuation under 35 U.S.C. 371 as a national patent application based on International Application Number PCT/IL2009/000817 filed on Aug. 20, 2009, which application claims priority to U.S. Provisional Application for Patents 61/098,774 filed on Sep. 21, 2008 and 61/180,901 filed on May 25, 2009, all of which are hereby incorporated by reference.

TECHNOLOGY FIELD

The present method and apparatus relate in general to the field of skin treatment and in particular to hair removal.

BACKGROUND

External appearance is important to practically every person. In recent years, methods and apparatuses have been developed for different cosmetic and dermatological treatments. Among these are hair removal, treatment of vascular lesions, wrinkle removal, skin rejuvenation and others. In some of these treatments, the skin surface is illuminated to heat deeper skin or tissue volumes to a sufficiently high temperature as to achieve a desired effect, which is typically in the range of 38-60 degrees Celsius. The effect may be weakening of the hair shaft or even hair follicle or root destruction.

Another desired effect may be hair re-growth retardation, which is typically achieved by illumination of an earlier depilated skin surface by laser, LED, Xenon lamp, Intense Pulsed Light (IPL), or incandescent lamp radiation, generally termed optical radiation. The optical radiation may have a single wavelength for example, lasers, or several wavelengths, or a broad band spectrum. The wavelengths are selected to be optimal for the color of the contrasted component of the treated skin segment, and are typically in the range of 400 to 1800 nm. The optical radiation, usually flashing or pulsed light, is applied to the skin with the help of an applicator having an aperture of a given dimension. In order to "cover" the entire skin surface, the aperture has to be moved from place to place, in a relatively accurate fashion on a step equal to at least one aperture dimension, so that no areas of the skin will be missed or treated twice. In order to avoid this, the individual visually tracks applicator location. The light pulses inevitably reach his/her eyes, disturb the individual, and affect the applicator location tracking and hair removal process. These devices achieve the desired effect only if a certain energy density is applied to the skin tissue. If the device is moved too quickly or too slowly across the skin, the device may be less efficacious or cause burns, respectively.

Concurrently a number of Radio Frequency (RF) to skin application based methods for treatment of deeper skin or tissue layers have been developed. In these methods, electrodes are applied to the skin and an RF voltage in pulse or continuous waveform (CW) is applied across the electrodes. The properties of the RF voltage are selected to generate RF induced current in a volume or layer of tissue to be treated. The current heats the tissue to the required temperature, which is typically in the range of 38-60 degrees Celsius. The temperature destroys or injures the hair follicle or root and delays further hair growth.

Equipment that combines light and RF treatment also exists. Usually this equipment is configured to illuminate a defined segment of a subject skin generally similar or equal to the surface of the aperture through which optical radiation is directed to the skin segment. The electrodes are typically located proximal to the periphery of the aperture and the RF typically may heat deeper tissue layers than those heated by light thus destroying/injuring hair bulbs and/or hair follicle. There is a delicate relation between the amount of RF energy and optical radiation applied to the same skin segment. Exceeding the optimal proportion between them leads to skin burns, whereas application of lower than optimal proportion RF energy and optical radiation does not bring the desired treatment results.

There is a need on the market for a small size, low cost, and safe to use apparatus that may be operated by the user enabling him/her to
i) avoid skin burns or non sufficient skin treatment results.
ii) avoid tediously looking at the treated area, during the course of treatment.

BRIEF SUMMARY

A skin treatment device for personal use for skin treatment and hair removal. The device includes an optical radiation providing module operating in pulsed or continuous operation mode, a hair removal mechanism, and a mechanism for continuously displacing the device across the skin. The hair removal mechanism may be a mechanical device and the mechanism for continuously displacing the device across the skin may be an optional mechanism. The user applies the device to the skin, operates the hair removal mechanism and optical radiation module and displaces the device manually or with the help of a built-in displacement mechanism across the skin segment to be treated. An optional displacement speed monitoring arrangement monitors the displacement speed and establishes the optical power as a function of the device displacement speed.

BRIEF LIST OF DRAWINGS

The apparatus and the method are particularly pointed out and distinctly claimed in the concluding portion of the specification. The apparatus and the method, however, both as to organization and method of operation, may best be understood by reference to the following detailed description when read with the accompanying drawings, in which like reference characters refer to the same parts throughout the different views. The drawings are not necessarily to scale, emphasis instead being placed upon illustrating the principles of the method.

DETAILED DESCRIPTION OF EXEMPLARY EMBODIMENTS

In the following detailed description, reference is made to the accompanying drawings that form a part hereof. This is shown by way of illustration of different embodiments in which the apparatus and method may be practiced. Because components of embodiments of the present apparatus can be in several different orientations, the directional terminology is used for purposes of illustration and is in no way limiting. It is to be understood that other embodiments may be utilized, and structural or logical changes may be made without departing from the scope of the present method and apparatus. The following detailed description, therefore, is not to be taken in a limiting sense, and the scope of the present apparatus and method is defined by the appended claims.

As used herein, the term "skin treatment" includes hair removal and treatment of various skin layers such as stratum corneum, dermis, epidermis, skin rejuvenation procedures, wrinkle removal, and such procedures as collagen shrinking or destruction.

The term "skin surface" relates to the most external skin layer, which may be stratum corneum.

Figure 1:
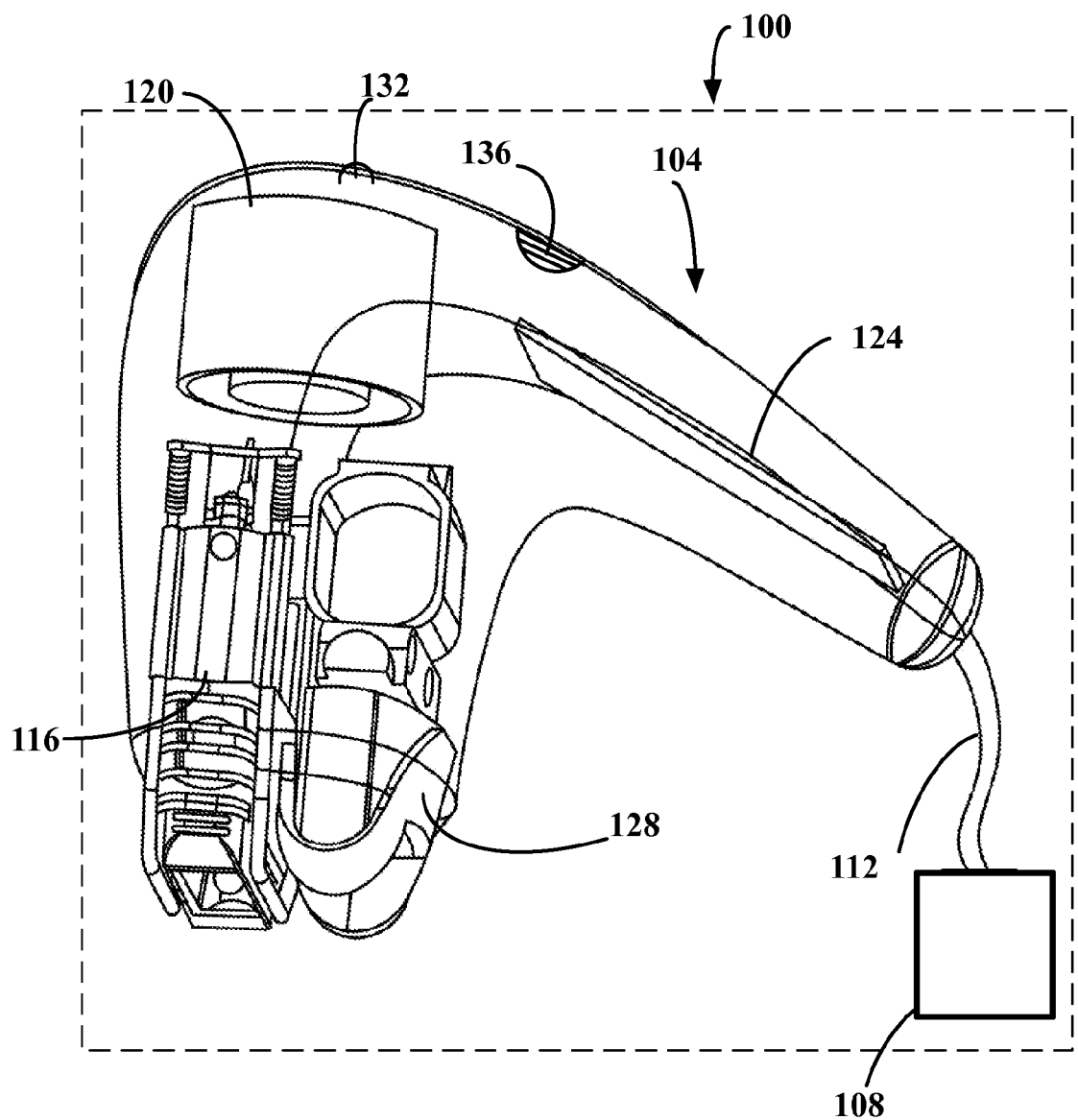
FIG. 1 is a schematic illustration of an exemplary embodiment of the apparatus for personal use for hair removal.
Figure 8:
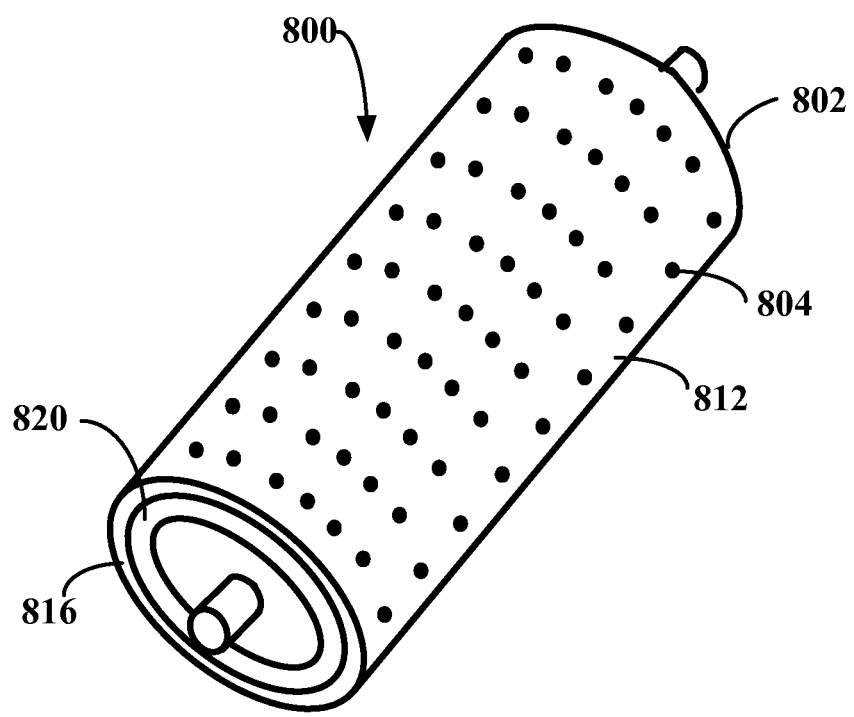
FIG. 8 is a schematic illustration of an exemplary disposable and exchangeable skin rejuvenation device for use with the present apparatus.

Reference is made to FIG. 1, which is a schematic illustration of an exemplary embodiment of the apparatus for personal skin treatment. Apparatus 100 includes an applicator or device 104 adapted for sliding movement on a subject skin; a base 108 comprising a controller, power supply module and a charge storage mechanism, such as a capacitor (not shown), where the power supply may include a transformer with or without current rectifier, and an umbilical cord 112 connecting between applicator 104 and base 108. Apparatus 100 may receive power supply from a regular electric supply network receptacle, or from a rechargeable or conventional battery. Applicator or device 104 is designed as a convenient to hold body (shown as having a transparent envelop) incorporating infrastructure 116, cooling means such as axial fan or blower 120, control circuit 124 controlling the operation of apparatus 100, and hair removal mechanism 128 attached to infrastructure frame 116 or assembled on a common frame. Hair removal mechanism 128 may be a variety of devices, such as a shaver head, a plucking or tweezing epilator like head, or razor, as a few non-limiting examples. Head 128 may be a detachable head or removeable. For safety reasons, the electric contacts for head 128 may be configured to activate the supply of electricity to the hair removal mechanism only when it is properly inserted in the appropriate location. In an additional embodiment, the hair removal mechanism may be replaced by a skin rejuvenation head (FIG. 8).

At least one visual status indicator 132, such as an LED, may be included on the device for informing or signifying to a user the operational status of the apparatus and/or skin treatment process parameter, and/or that a mechanism is attached to device 104, etc. At least one optional audio status indicator 136 such as a buzzer signaling to the user the status of skin treatment process parameters is also attached to device 104 or located in base 108.

Figure 2:
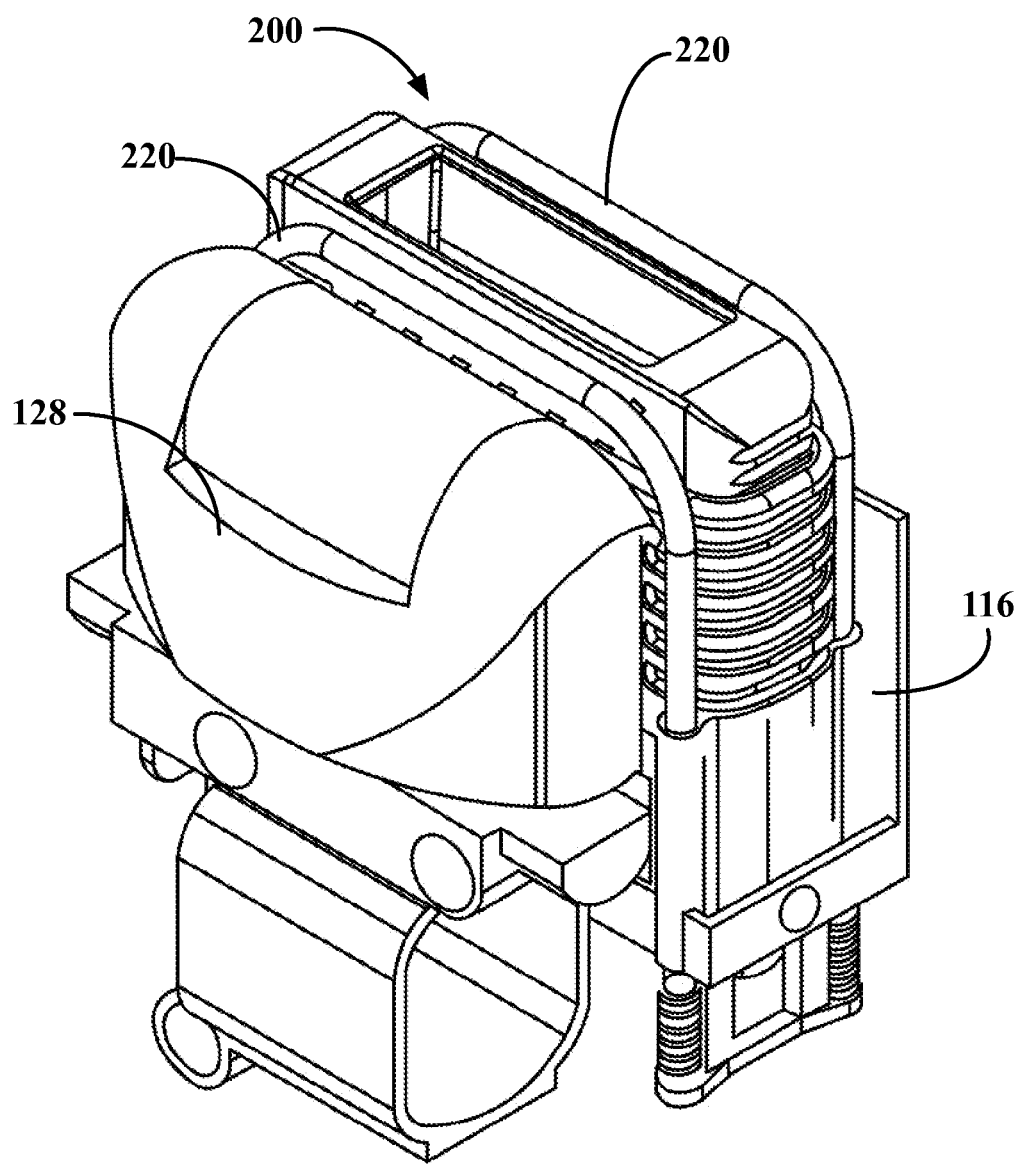
FIG. 2 is a schematic illustration of an exemplary embodiment of the infrastructure assembly of the applicator or device for personal use for hair removal.

FIG. 2 is a schematic illustration of an exemplary embodiment of the infrastructure assembly of the applicator or device for personal skin treatment. Mounted on the infrastructure 116 is an optical radiation providing module 200, a mechanism or arrangement shown in FIGS. 5A-5C for continuously displacing device 104 across the skin, a displacement speed monitoring mechanism (FIG. 5A), and a safety switch (FIG. 3) mounted on the infrastructure frame 116 (FIG. 1) and activated by the radiation providing module 200 (FIG. 2). Hair removal mechanism 128, operatively configured to mechanically remove hair from the treated or target segment of the skin, is attached to infrastructure frame 116. Optionally, a pair of electrodes 220 may be attached to infrastructure frame 116.

Figure 3:
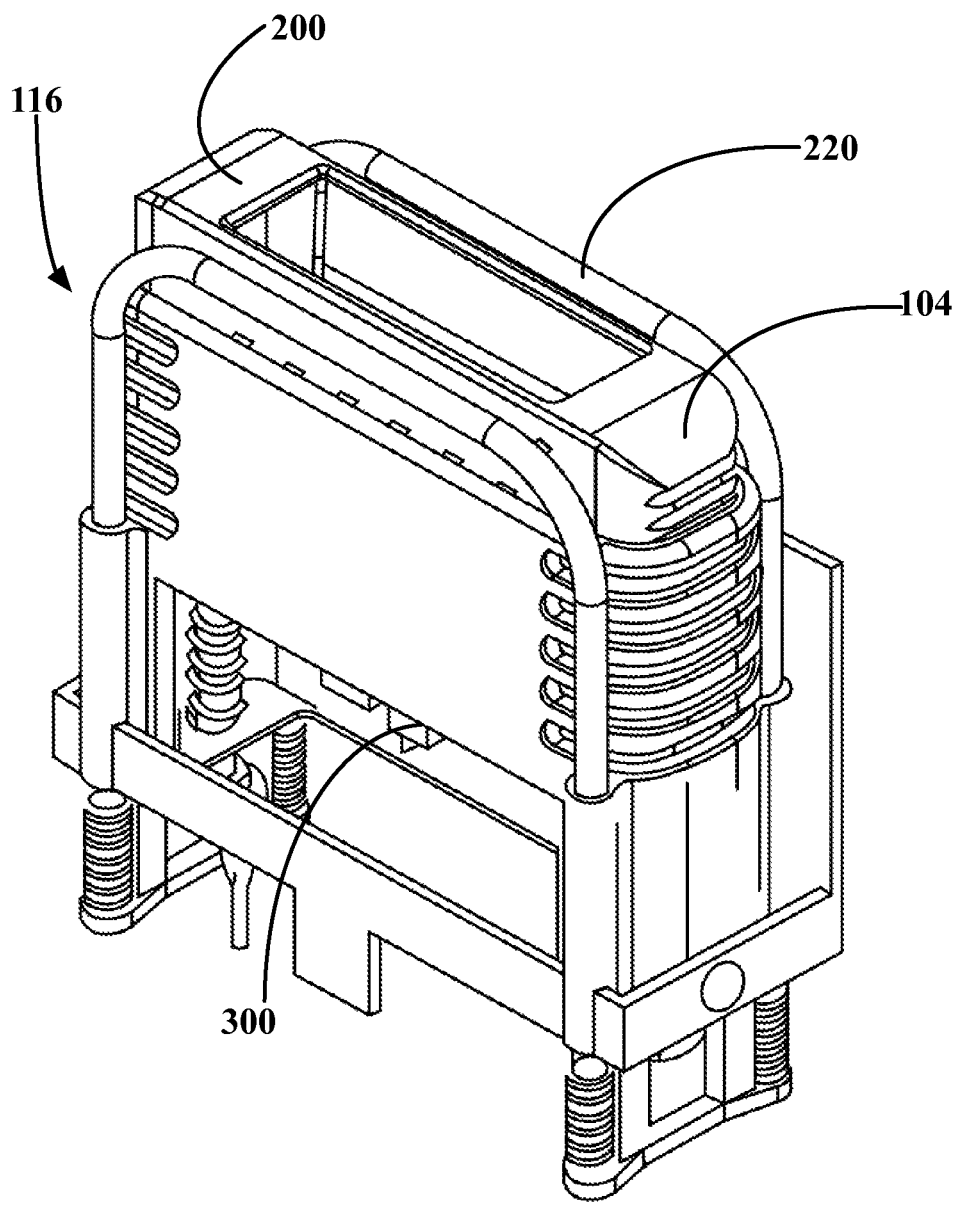
FIG. 3 is a schematic illustration of an exemplary embodiment of the infrastructure assembly shown without the hair removal mechanism.

FIG. 3 is a schematic illustration of an exemplary embodiment of the infrastructure frame 116 assembly shown without the hair removal mechanism 128 (FIG. 1). It illustrates a safety switch 300 mounted on infrastructure frame 116 and device 104 displacement direction sensor 528 shown in FIG. 5A. Insertion of radiation providing module 200 (FIG. 2), into its location in frame 116 activates safety switch 300. This prevents idle or erroneous operation of module 200. For example no high voltages will be present and "alive" in the electrodes of the applicator 104 so that users are not subject to high voltage danger if the disposable cartridge is removed.

According to some embodiments of the disclosure, an RFID device is connected to control circuit 124 (FIG. 1). The RFID device is preloaded with a maximal number of pulses to be emitted before the radiation providing module 200 has to be replaced and decreases the count with every emitted pulse. Alternatively, the RFID device is preloaded with a total energy that may be applied to the skin in a single treatment before the radiation providing module 200 (FIG. 2) has to be replaced. The RFID device may also serve as an additional safety measure, where the control circuit 124 prevents the radiation providing module 200 from emitting pulses if the RFID is not identified, namely the radiation providing module 200 has not been installed correctly.

In an additional embodiment, a 1024 Bit 1-Wire EEPROM such as DS2431 commercially available from Maxim/Dallas Semiconductors, Inc., Sunnyvale, Calif. 94086 U.S.A. 1-Wire EEPROM operating as a counter can be assembled on the control printed circuit 124 that among others controls the radiation providing module 200. Similar to the RFID, the counter may be pre-loaded with the desired information. The same 1-Wire EEPROM may function for radiation providing module 200 authenticity identification.

Figure 4A:
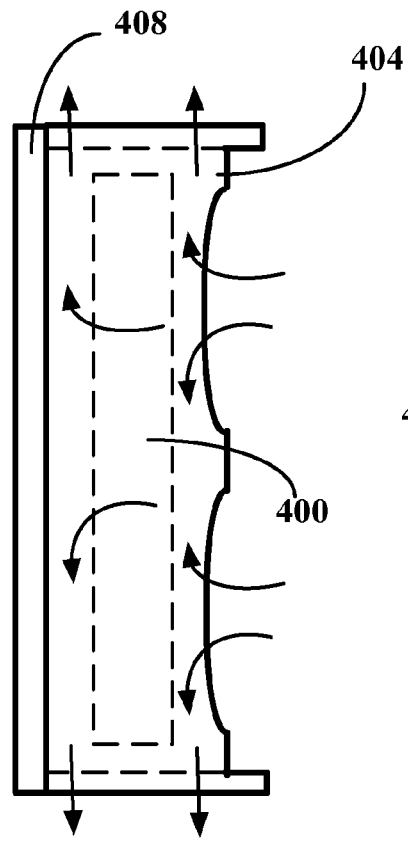
FIG. 4A, FIG. 4B and FIG. 4C are respectively a side elevation view, top plan view and end elevation view of an exemplary embodiment of the reflector of the optical radiation providing module and its cooling method.
Figure 4B:
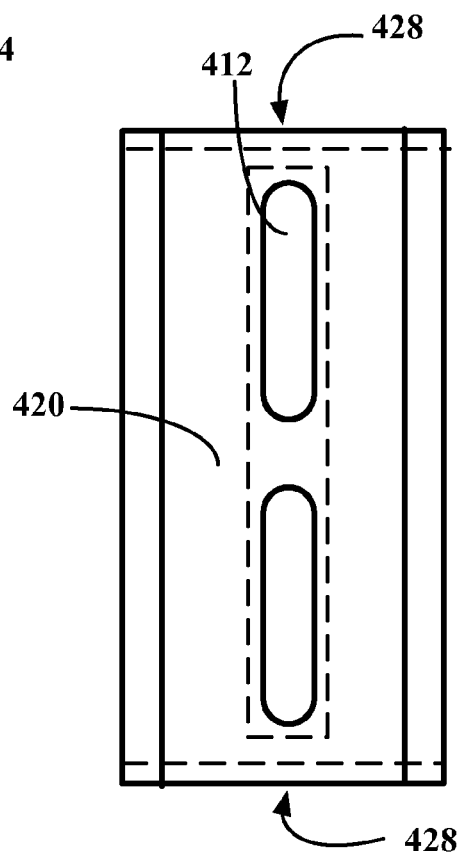
Figure 4C:
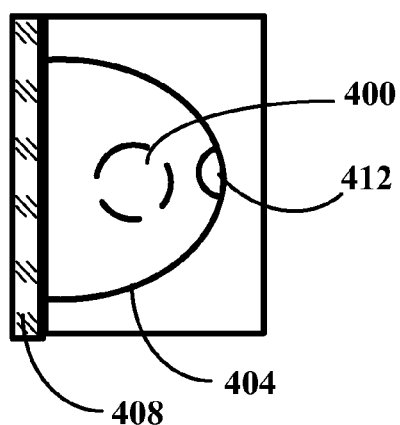

FIG. 4A, FIG. 4B and FIG. 4C are respectively a side elevation view, top plan view and end elevation view of an exemplary embodiment of the reflector of the optical radiation-providing module and its cooling method. Module 200 is implemented as a disposable cartridge including a source of optical radiation 400, a reflector 404 configured to reflect the emitted optical radiation to the segment of the skin to be treated, and a dielectric coated protective window 408. Window 408 defines the aperture through which the optical radiation is emitted to the skin. The source of optical radiation 400, shown in broken lines, may be an incandescent lamp such as AGAC 4627 high power density Xenon flash lamp commercially available from PerkinElmer Optoelectronics Wenzel-Jaksch Str. 31 65199 Wiesbaden, Germany or other sources such as, but not necessarily limited to, an LED, laser diode, solid state laser, a gas laser, or a Xenon IPL (Intense Pulsed Light) lamp.

Reflector 404 is a prismatic case or body with flat facets and polygonal cross section or a tubular case or body with an optional curvature of second or higher power. It may be a simple round cylinder cross section, a parabolic cross section or any other cross section allowing the optical radiation to be concentrated and distributed uniformly across the aperture of window 408 through which the optical radiation is emitted to the skin. The dielectric coating of window 408 is selected such as to transmit the relevant sections of optical radiation spectrum to the treated segment of the skin and reflect the other. Reflector 404 has openings 412 allowing air passage inside the reflector. Openings 412 are located about the apex of reflector 404. The dielectric coated protective window 408 located adjacent or attached to the open longitudinal section of reflector 404 forms, with the reflector 404, an air-conducting channel 420 bound on one side by reflector 404 and on the other side by window 408. A part of the stream of cooling air 424 generated by a cooling element such as an axial fan 120 (FIG. 1) enters channel 420 through openings 412. It is directed into the air-conducting channel 420 along the source of optical radiation 400 shown in broken lines and cools it. Butt end openings 428 of reflector 404 terminate air-conducting channel on both of the ends and serve as cooling air exhaust openings. The area of air exhaust openings 428 is at least equal or larger to the area of openings 412 allowing air passage into inner part of reflector 404 and air conducting channel 420. The other part of cooling air stream 424 flows around the external section of reflector 404 and cools the outer section of reflector 404.

Figure 10A:
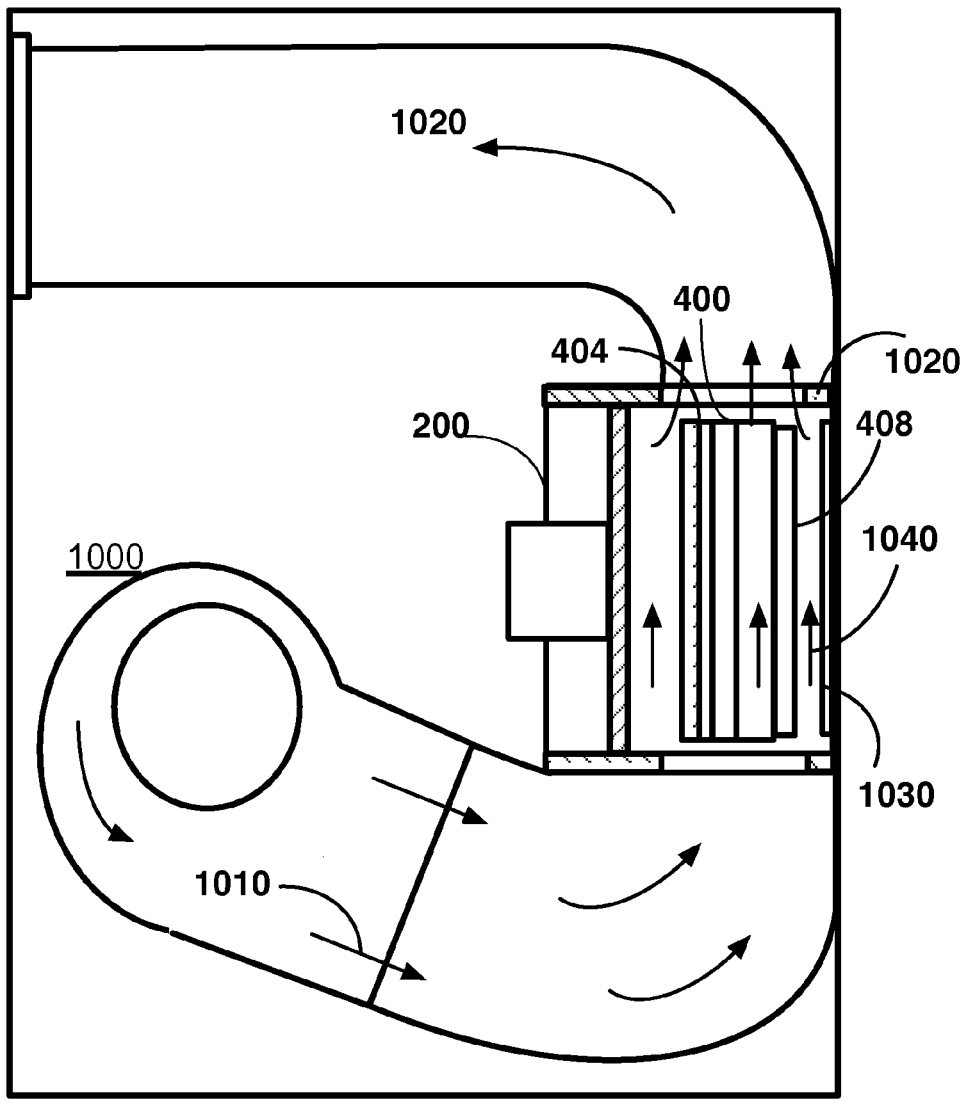
FIG. 10A and FIG. 10B are schematic illustrations of a cross section of another exemplary embodiment of the optical radiation providing module and its cooling method.
Figure 10B:
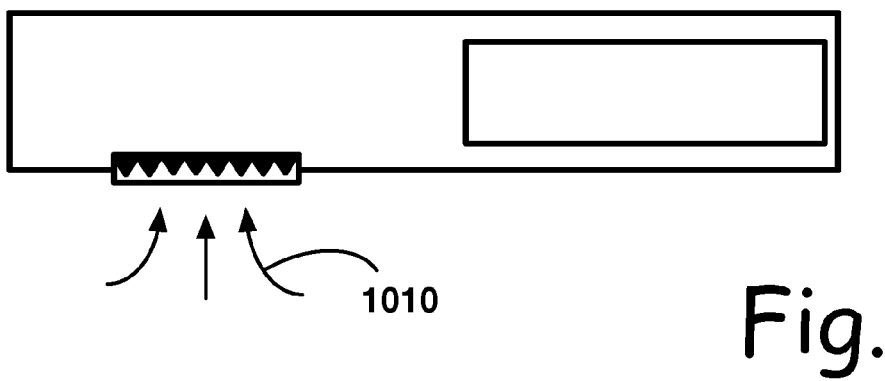

According to some embodiments of the disclosure, as depicted schematically in FIG. 10A and FIG. 10B, the cooling means comprises a rotary blower 1000. Blower 1000 blows air shown by arrows 1010 into one side of the optical radiation providing module 200 (FIG. 2), where the air flows in parallel (along) to the source of optical radiation 400 and the reflector 404 (FIG. 4A, FIG. 4B and FIG. 4C) and emerges from the opposite side as shown by arrows 1020 of the optical radiation providing module 200.

Figure 11:
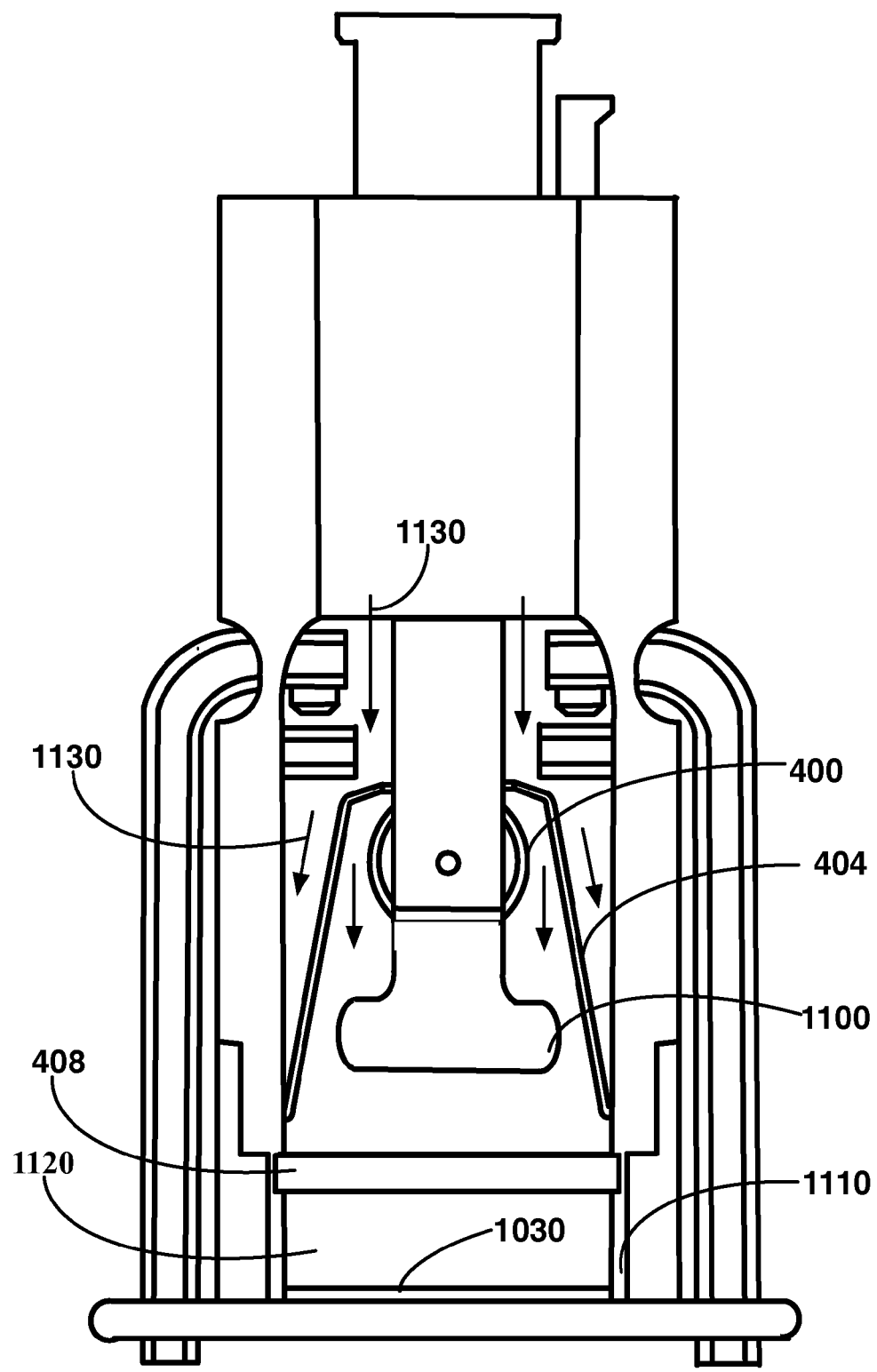
FIG. 11 is a schematic illustration of an additional exemplary embodiment of the optical radiation providing module and its cooling method.

According to some embodiments of the disclosure, as also depicted schematically in FIG. 10A and FIG. 10B, a second glass window 1030 is installed in parallel to window 408 and part of the cooling air blown by the blower 1000 and marked by arrow 1040 flows between the two windows 408 and 1030. A slanted lamp electrode 1100, as shown in FIG. 11, may be installed on the air intake side of the optical radiation source 400, to enhance air flow in the direction of the windows. Arrows 1130 schematically illustrate the cooling air flow inside and outside reflector 404 and between the widows 408 and 1030. Reflector 404 is shown in FIG. 11 as a prismatic structure.

According to some embodiments of the disclosure, a fan 120, as depicted in FIG. 1, may also be used to cool the air between the two glass windows. It was experimentally proven that three or more windows parallel to window 408 with cooling air flow between them provide a good thermal isolation and the part of the device being in contact with the skin almost does not change its temperature.

According to some embodiments of the disclosure, a thermal sensor 1050, such as a thermistor, or any other type of temperature measuring means may be installed on either the inflow or the outflow end of the cooling air, as a safeguard against overheating in case of a malfunction of the cooling means.

Windows 408 and 1030 may be made of pyrex, sapphire, quartz, or specially treated borosilicate glass. Window 1030 or both windows may be coated with a dielectric coating serving as a filter for reflecting back undesired wave lengths, such as UV and certain IR wavelengths, emitted from the optical radiation source 400.

According to some embodiments of the disclosure, as also shown in FIG. 11, two reflectors (1110, 1120) may be mounted between the two windows (1030, 408), on both sides thereof, to prevent light scattering outside the treatment area.

The architecture of optical radiation providing module 200 and the method of cooling it allows a compact and effective optical radiation source to be produced and provide sufficient power for skin treatment. Module 200 may operate in pulsed or continuous operation mode. It is known that low repetition rate optical radiation or light pulses are annoying to the user who may be constantly visually tracking the applicator location. In order to ease the user's sensation, the optical radiation source may emit a number of low power light pulses interleaved between high power treatment pulses, increasing the repetition rate of the light pulses and alleviating the annoying and eye disturbing effects of low repetition rate light pulses.

Figure 5A:
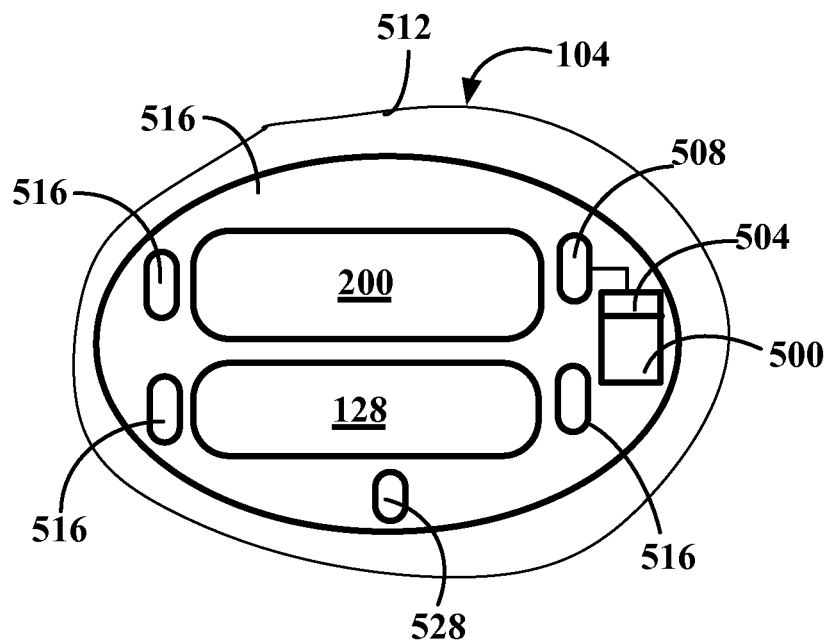
FIG. 5A is a schematic illustration of an exemplary embodiment of the device displacement mechanism.

FIG. 5A is a schematic illustration of an exemplary embodiment of the device displacement mechanism. It illustrates a bottom view of an exemplary mechanism for continuously displacing device 104 across the skin. The mechanism includes a DC motor 500 of suitable size and power coupled by means of one or more gears 504 to one or more drive wheels 508 or a caterpillar type track. The user attaches device 104 to the skin 512 (FIG. 5B) and applies minimal force preventing the device from falling of the skin. Device 104 may have additional auxiliary wheels 516 in any proper amount, as required. Operation of DC motor 500 allows displacing device 104 across skin 512 with variable speed. A wheel or roller 528 of a known diameter is in contact with the skin. The roller 528 rotates as the device moves. Measuring the rotation speed of roller 528 makes it possible to determine the device displacement speed by methods known to those skilled in the art. Alternatively, one of the wheels 508 or 516 may have a known diameter.

Figure 5B:
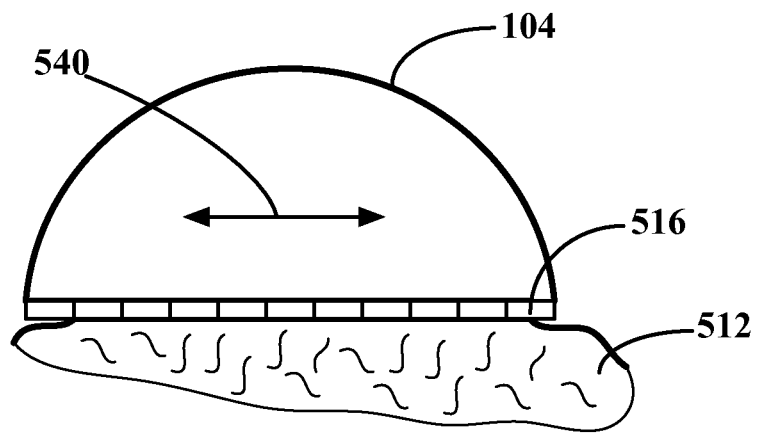
FIG. 5B is a schematic illustration of another exemplary embodiment of the device displacement mechanism.
Figure 5C:
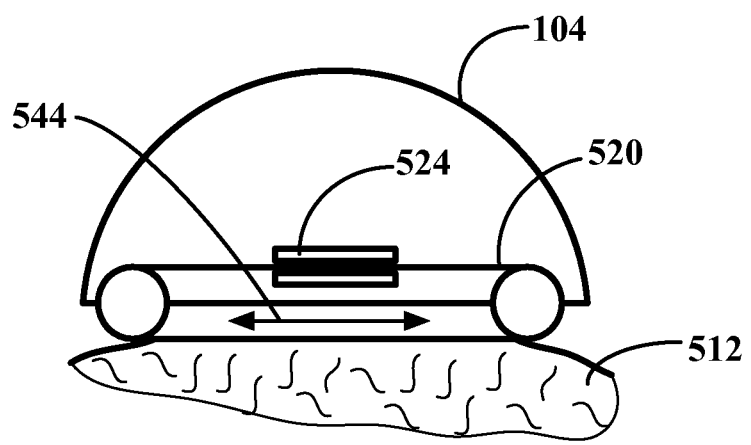
FIG. 5C is a schematic illustration of an additional exemplary embodiment of the device displacement mechanism.

In another exemplary embodiment of the device displacement mechanism shown in FIG. 5B a peristaltic piezoceramic motor 516 implemented as a caterpillar type track displaces device 104 across the skin 512 as illustrated by arrow 540. In still an additional exemplary embodiment of the device displacement mechanism illustrated in FIG. 5C a belt 520 driven by a piezoceramic motor 524 or other type of motor displaces device 104 across the skin 512 as shown by arrow 544.

Figure 6A:
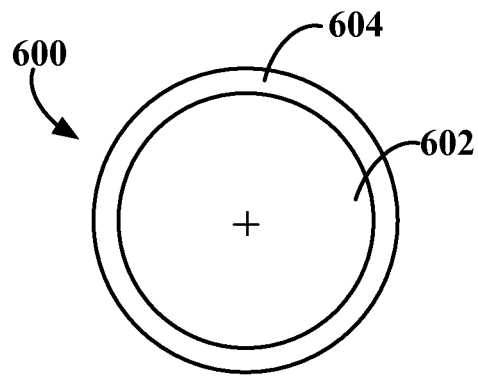
FIGS. 6A, 6B and 6C, are schematic illustrations of exemplary embodiments of a device displacement speed sensing mechanism.
Figure 6B:
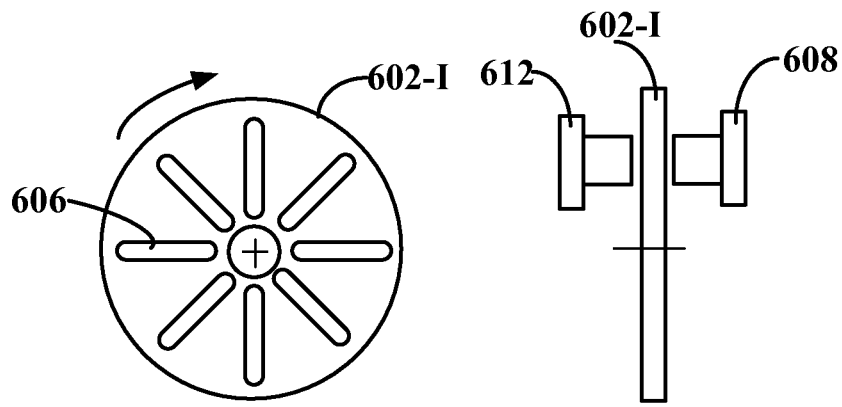
Figure 6C:
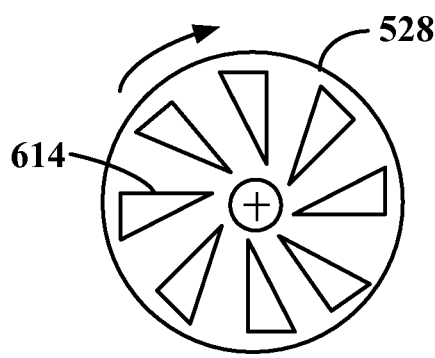

The device displacement mechanisms described above allow displacing device 104 with variable speed to be adapted to different skin treatment conditions. This however requires the ability to sense or monitor, and correct the device displacement speed. FIGS. 6A, 6B and 6C, are schematic illustrations of exemplary embodiments of a device displacement speed and displacement direction sensing arrangement. In FIG. 6A, device 104 (FIGS. 1 and 5) displacement speed monitoring arrangement 600 may be a rotating wheel 602 or roller of known diameter being in permanent contact with skin 512. Wheel 602 may have an O-ring 604 tensioned on the periphery of wheel 602. Displacement speed monitoring arrangement 600 may be implemented as a wheel 602-I (FIG. 6B) with openings 606 and located between a LED 608 with a detector 612 configured to generate pulses when an opening passes between them. Alternatively, the wheel may be connected to a speed measurement device for example, such as a tachometer being in communication with control circuit 124. According to the speed-readings, control circuit 124 (FIG. 1) may change the displacement speed of device 104. In an alternative embodiment, an arrangement similar to an optical mouse monitors device 104 displacement speed.

Continuous sensing of the device displacement speed or velocity and direction of advance, coupled with visual or audio signals informing the user on the status of the treatment, releases the user from the annoying task of constantly tracking the applicator location visually. The user still has to ascertain that applicator displacement velocity is in accordance to the desired applicator velocity related to at least the radiation source pulse repeat rate and the active size of the aperture. The visual signal indicator and audio signal indicator provide the user the information necessary for deciding on the skin treatment status, and the user is free from memorizing the location of the previously treated strip or strips.

Direction displacement sensor may be a wheel 528 (FIG. 5) that may have asymmetric openings 614 and an LED 608 with a detector 612 configured to generate pulses when an opening passes between them. Alternatively, one of the wheels 508 or 516 may have asymmetric openings. Depending on the displacement direction the pulses caused by modulation of LED radiation by the openings 612 will have a different rise time, indicating on the displacement direction. When treatment of the skin segment is completed the operator changes the displacement direction of the applicator.

Figure 7:
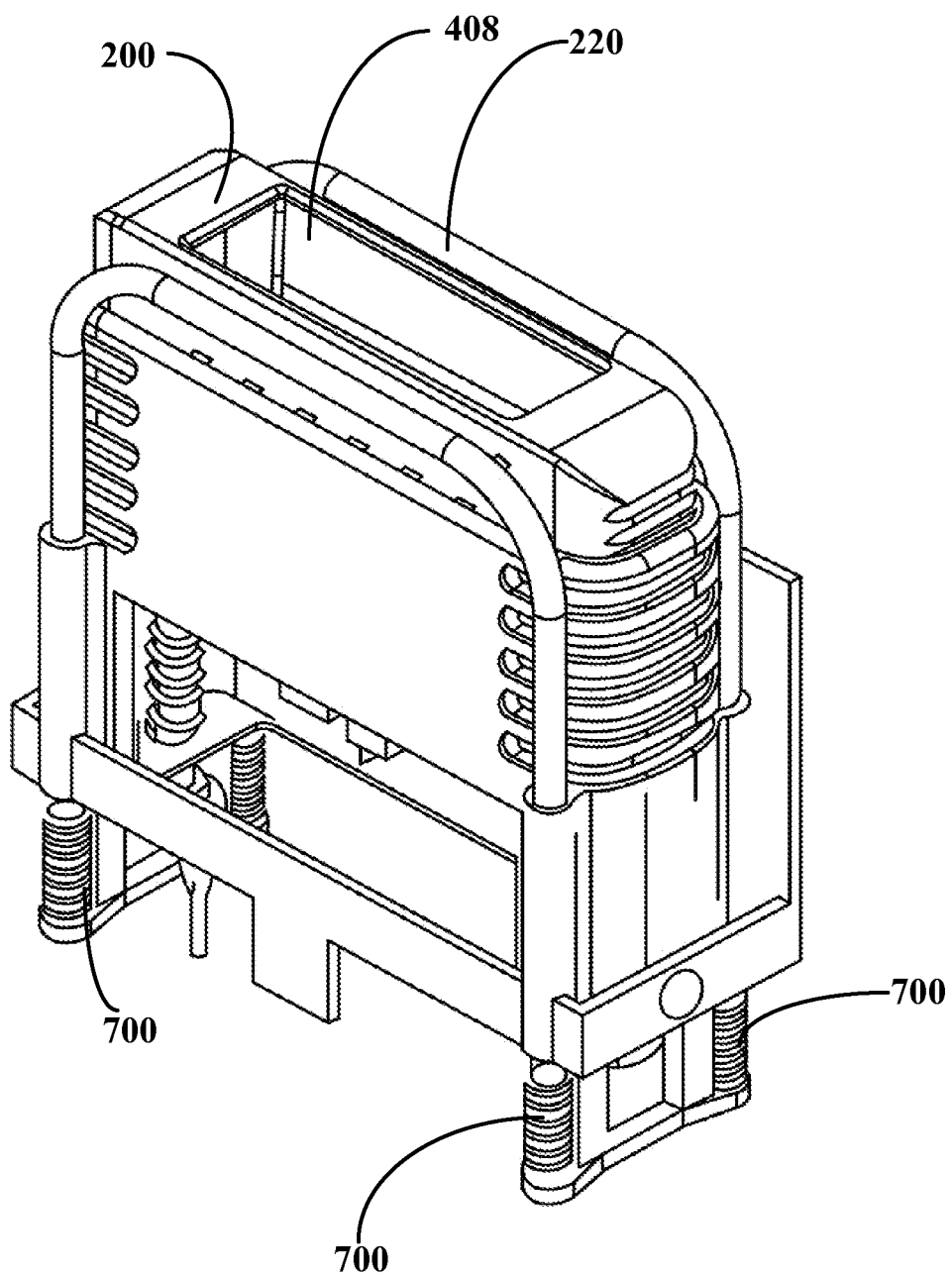
FIG. 7 is a schematic illustration of an exemplary embodiment of the electrodes of the device for personal use for hair removal.

FIG. 7 is a schematic illustration of an exemplary embodiment of the electrodes of the hair removal device for personal use. Skin treatment device 104 optionally includes a pair of optionally detachable electrodes 220 (FIG. 2) operatively configured to apply RF energy to a segment of the skin. RF electrodes 220 have an elongated body arranged along at least one side of protective window or aperture 408 (FIG. 4A, FIG. 4B and FIG. 4C). RF electrodes 220 are suspended on springs 700 with respect to infrastructure frame 116. Alternatively, electrodes 220 may comprise solid metal strips 710 attached to the external side of the optical radiation providing module 200 housing. Metal coating deposited on suitable, maybe even plastic, surfaces of module 200 may also serve as electrodes 220. During skin treatment RF electrodes 220 are in permanent contact with skin and accurately follow the skin topography. RF electrodes 220 or 710 may have a bare metal surface and be in conductive coupling with the skin, or may be dielectric coated electrodes and be in capacitive coupling with the skin.

FIG. 8 illustrates an exemplary disposable and exchangeable skin rejuvenation device for use with the present apparatus. Device 800 may be mounted instead of hair removal mechanism 128. Device 800 is a cylindrical or other three-dimensional shape carrier 802 on the surface of which are dome shaped conductive elements 804 configured such that domes 804 protrude from external surface 812 of the carrier 802. Carrier 802 may be produced by stretching a flexible substrate over a carcass. This may be a solid cylinder or a squirrel cage type structure. Sides 816 of carrier 802 may bear contact strips 820 through which RF voltage can be supplied to domes 804. Such configuration of the carrier allows applying and translating it over relatively large segments of the skin. In the context of the present disclosure, "large segment of skin" signifies a segment of skin dimensions which exceed the dimensions of the surface of the carrier, or circumference of the surface of the contact electrode or electrodes carrier. Carrier 802 has a rotational symmetry and can be easily repositioned for treatment of a neighboring skin segment by rolling it on the skin, thus providing a reasonable time for thermal relaxation of the skin segment treated earlier, and returned back to the same skin segment treated previously. The repositioning of the carrier does not leave segments or patches of the skin that were not treated and eliminates the residual patchwork type skin pattern. This type of skin treatment actually represents a continuous skin surface treatment process. Carrier 802 may be a reusable or disposable part.

Figure 9:
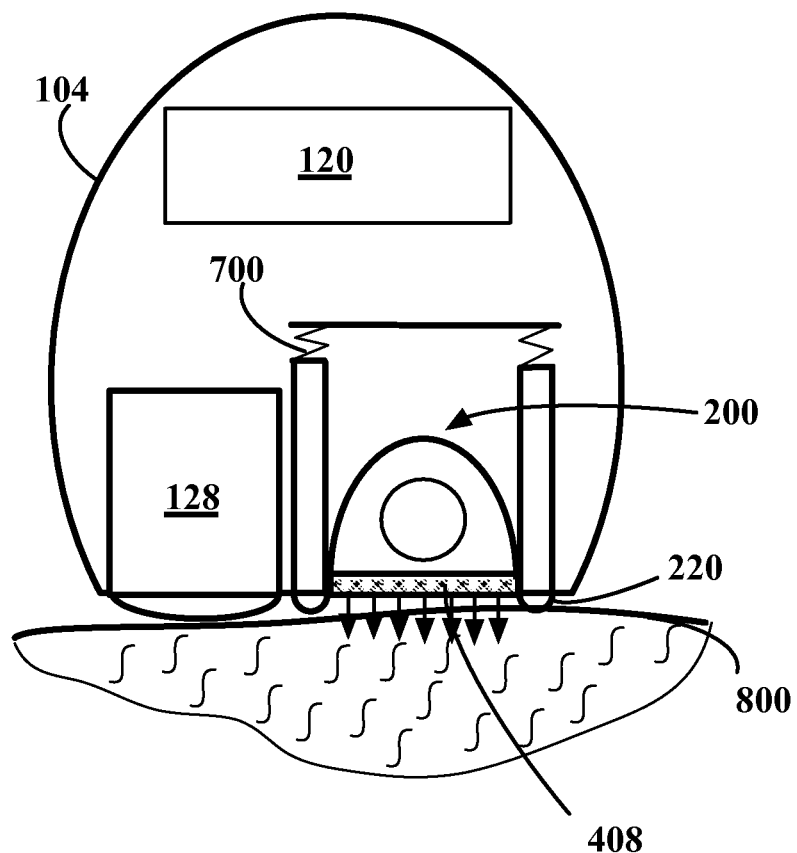
FIG. 9 is a schematic illustration of another exemplary method of skin treatment using the present device and apparatus.

FIG. 9 is a schematic illustration of an exemplary method of skin treatment using the present device and apparatus. For skin treatment, device 104 is applied to a segment of skin 900 to be treated, enabling permanent or at least mostly permanent contact between the RF electrodes 220 (FIG. 2) and the skin. Optical radiation providing module 200 is activated, and the mechanism for continuously displacing the device across the skin displaces device 104 in a desired direction, for example, along the segment of the skin to be treated. In one embodiment, optical radiation is directed through aperture 408 to irradiate a segment of skin to be treated by a constant optical radiation power, supplied in continuous or pulsed mode, and displacement speed monitoring arrangement 600 (FIG. 6) sets a proper displacement speed. The displacement speed—optical radiation power dependence may be prepared and loaded as a look-up-table (LUT) into control circuit 124. As the treatment progresses and device 104 advances across the skin, it reaches the border of the skin segment to be treated. As device 104 reaches the end of the treated or shaved skin segment, the user manually repositions device 104 on the next segment of skin to be treated or on another non-treated segment of the skin and sets it for displacement into the same or opposite direction. The danger of causing skin burns by treating the same segment of skin twice is reduced, since there is some time for the skin to cool down between successive skin treatments by device 104. Optical radiation retards future hair growth on the treated segment of the skin by heating hair follicle. RF energy applied to the same skin segment heats deeper skin layers where hair bulbs and follicles are located, and the heat generated by the RF energy destroys them, enhancing the hair removal process performed by the optical radiation.

In an additional exemplary method of skin treatment using the present device and apparatus, the user applies the skin treatment device 104 to a skin segment from which hair has to be removed. The hair is removed from the skin segment by mechanical means, for example by shaving it or plucking it. Following mechanical hair removal, optical radiation of proper power and wavelength is applied to the same segment of skin that was treated. Optionally, RF energy may be applied to the same segment of skin. Application of optical radiation and RF energy retards further hair growth and removes hair residuals left after mechanical hair removal from the treated skin segment. Similar to the earlier disclosed method the device treating the skin segment displaces itself automatically from a treated skin segment to another untreated skin segment.

A number of embodiments have been described. Nevertheless, it will be understood that various modifications may be made without departing from the spirit and scope of the method. Accordingly, other embodiments are within the scope of the following claims:

What is claimed is:

1. A skin treatment device for personal use, said device comprising:
a hair removal mechanism operatively configured to mechanically remove hair from the target skin segment, wherein said hair removal mechanism is at least one of a group of a shaver, an epilator, and a razor;
an optical radiation providing module operating in pulsed or continuous operation mode, wherein when the radiation providing module operates in pulse mode it radiates a number of low power pulses interleaved between high power treatment pulses, configured to remove from said skin segment hair residuals left after mechanical hair removed and wherein the optical radiation providing module comprises:
a source of optical radiation;
a reflector configured to reflect the emitted optical radiation to the segment of the skin; and
a cooling means operatively adapted to cool the source of optical radiation;
characterized in that the optical radiation providing module further comprises:
at least one dielectric coated protective window, wherein the at least one dielectric coated protective window is located adjacent an open longitudinal section of the reflector and forms with the reflector an air-conducting channel bound on one side by the reflector and on the other side by the dielectric coated protective window; wherein the reflector is a tubular or prismatic case configured to have openings located about the apex of the reflector and allowing air passage inside the reflector in a direction perpendicular to the source of optical radiation and air exhaust openings are located at the open butt ends of the reflector such that air directed into the air-conducting channel by the cooling means and through openings provide cooling for the source of optical radiation;
wherein the cooling means are operatively configured to form an air flow in the air conducting channel by directing an air stream inside the reflector along the source and exhausting the air through the exhaust openings.

2. The skin treatment device according to claim 1, further comprising a mechanism for continuously displacing the device across the skin.

3. The skin treatment device according to claim 1, wherein the optical radiation providing module is a disposable cartridge.

4. The skin treatment device according to claim 2, wherein the optical radiation providing module is a disposable cartridge.

5. The skin treatment device according to claim 1, wherein the cooling means are one of a group consisting of a fan and a blower.

6. The skin treatment device according to claim 2, wherein the cooling means are one of a group consisting of a fan and a blower.

7. The skin treatment device according to claim 3, wherein the cooling means are one of a group consisting of a fan and a blower.

8. The skin treatment device according to claim 1, wherein the cooling means are operatively configured to form an air flow along the source of optical radiation.

9. The skin treatment device according to claim 2, wherein the cooling means are operatively configured to form an air flow along the source of optical radiation.

10. The skin treatment device according to claim 3, wherein the cooling means are operatively configured to form an air flow along the source of optical radiation.

11. The skin treatment device according to claim 1, wherein the source of optical radiation is one of a group of incandescent lamp, LED, laser diode, solid state laser, a gas laser, or a Xenon IPL lamp.

12. The skin treatment device according to claim 1, wherein the dielectric coated protective window serves as a filter and defines the spectrum of the radiation directed to the skin and the aperture through which the radiation is emitted to the skin.

13. The skin treatment device according to claim 1 further comprising a pair of electrodes operatively configured to apply RF energy to a segment of the skin.

14. The skin treatment device according to claim 1, wherein the cooling means are designed to form an air flow between two dielectric coated protective windows.

15. The skin treatment device according to claim 13, wherein said pair of electrodes is one of a group consisting of metal strips or metal coated nonconductive material and wherein the RF electrodes have an elongated body arranged along at least one side of the protective window.

16. The skin treatment device according to claim 15, wherein the RF electrodes are at least one of a group of uncoated or dielectric coated electrodes.

17. The skin treatment device according to claim 13, wherein the RF electrodes are adapted to be in contact with the skin during treatment and follow skin topography.

18. The skin treatment device according to claim 2, wherein the mechanism for continuously displacing the device across the skin is at least one of a group consisting of a DC motor with a gear, a peristaltic piezoceramic motor, or a caterpillar driven by a piezoceramic motor.

19. A method of safe skin treatment, said method comprising:
applying a skin treatment device according to claim 2 to a skin segment from which hair has to be removed;
removing the hair from the skin segment by means of said hair removal mechanism;
applying to said skin segment optical radiation of proper power and wavelength by means of the source of optical radiation in combination with the reflector, thereby removing from said skin segment hair residuals left after mechanical hair removal;
generating a stream of cooling air by a cooling element, said cooling air entering an air-conducting channel bound on one side by the reflector and on the other side by a dielectric coated window through openings, and
displacing the device automatically from a treated skin segment to another not treated skin segment by means of the mechanism for continuously displacing the device across the skin.

* * * * *